(12) United States Patent
Olsson et al.

(10) Patent No.: US 7,425,242 B2
(45) Date of Patent: Sep. 16, 2008

(54) METHOD FOR PRODUCING PREFASTENED ABSORBENT PRODUCT WITH ELASTIC RECLOSABLE SIDES

(75) Inventors: Ken Olsson, Frölunda (SE); Marie Johansson, Mölnlycke (SE); Helena Corneliusson, Bohus (SE)

(73) Assignee: SCA Hygiene Products AB, Gothenburg (SE)

( * ) Notice: Subject to any disclaimer, the term of this patent is extended or adjusted under 35 U.S.C. 154(b) by 463 days.

(21) Appl. No.: 11/197,345

(22) Filed: Aug. 5, 2005

(65) Prior Publication Data
US 2006/0027306 A1 Feb. 9, 2006

Related U.S. Application Data

(62) Division of application No. 10/403,299, filed on Apr. 1, 2003.

(60) Provisional application No. 60/368,978, filed on Apr. 2, 2002.

(51) Int. Cl.
*A61F 13/15* (2006.01)

(52) U.S. Cl. .................. 156/204; 156/226; 156/227

(58) Field of Classification Search ................ 156/202, 156/204, 226, 227
See application file for complete search history.

(56) References Cited

U.S. PATENT DOCUMENTS

| | | | |
|---|---|---|---|
| 4,940,464 A | 7/1990 | Van Gompel et al. | |
| 5,370,634 A | 12/1994 | Ando et al. | |
| 5,496,298 A | 3/1996 | Kuepper et al. | |
| 5,531,732 A * | 7/1996 | Wood | 604/391 |
| 5,685,874 A | 11/1997 | Buell et al. | |
| 6,113,717 A | 9/2000 | Vogt et al. | |
| 6,447,497 B1 | 9/2002 | Olson | |
| 6,508,797 B1 | 1/2003 | Pozniak et al. | |
| 6,761,711 B1 | 7/2004 | Fletcher et al. | |
| 2004/0092903 A1 | 5/2004 | Olson et al. | |

FOREIGN PATENT DOCUMENTS

| | | |
|---|---|---|
| EP | 0 570 980 A1 | 11/1993 |
| GB | 2 267 024 A | 11/1993 |
| WO | 95/29657 A1 | 11/1995 |
| WO | 96/31178 A2 | 10/1996 |
| WO | 99/65438 A1 | 12/1999 |
| WO | 00/35396 A1 | 6/2000 |
| WO | 00/37005 A2 | 6/2000 |

* cited by examiner

*Primary Examiner*—Richard Crispino
*Assistant Examiner*—Barbara J. Musser
(74) *Attorney, Agent, or Firm*—Buchanan Ingersoll & Rooney PC

(57) ABSTRACT

An absorbent prefastened product in the form of a disposable pants diaper is provided with a side closure arrangement on each side. The side closure includes front and rear side flaps having elastic portions where an inner surface of a rear side flap is overlapped and welded to an outer surface of a front side flap. Each side flap is also provided with one part of a releasable fastening system located such that the weld is located on at least one of the elastic portions and such that it lies inward of the releasable fastening system in the prefastened state. A method of forming the absorbent product is also provided, in which an overlapped attachment is formed by joining front and rear side flap members together and attaching the side flap members to an absorbent chassis member.

5 Claims, 9 Drawing Sheets

METHOD FOR PRODUCING PREFASTENED ABSORBENT PRODUCT WITH ELASTIC RECLOSABLE SIDES

This application is a division of U.S. application Ser. No. 10/403,299, filed Apr. 1, 2003, which claims priority to U.S. Provisional Application No. 60/368,978 filed Apr. 2, 2002, and entitled "Prefastened Absorbent Product with Elastic Reclosable Sides and Method for Producing Same," the entire contents of which is hereby incorporated by reference.

FIELD OF THE INVENTION

The present invention relates to an absorbent product for absorbing human exudate, such as a diaper or training pants and more particularly, to a disposable pants diaper which is manufactured in a closed state, i.e. a prefastened state, ready to be pulled on for wearing, yet which comprises side closures which can be opened and reclosed.

BACKGROUND TO THE INVENTION

Disposable training pants are well known and several different designs are available. For example, disposable training pants having front and rear portions fixedly attached together are known from WO-A-95/29657 and WO-96/31178. These designs provide adjustability of the waistband size to a range of users due to various elastic arrangements, but they must be removed like a normal pair of pants since the waist regions are formed with substantially continuous waistbands.

WO-A-00/35396 also discloses training pants with side panels which can be elastic. The side panels are formed overlapped and attached together in a prefastened state by means of releasable fastening means. The side closures further include an adhesive between them, in order to limit accessibility to the reclosable fastening means. The adhesive is placed so as to connect the outer flap of the overlapped flaps to the inner flap at a distal end location of the outer flap beyond the location of the releasable fastening means thereon. This provides a child-safety function. The adhesive bond is then opened to gain access to the reclosure element. Since the adhesive must allow access to the reclosure means without destruction of the side panels during opening of the adhesive bond (otherwise the product would be ruined) a low bond force must be used for the adhesive. In preferred embodiments the glue should remain tacky to allow repeated opening and reclosure.

GB-A-2 267 024 discloses a prefastened absorbent product providing the possibility of rupture of the side seams for removal or inspection of the product, and then the further possibility of re-closure. The absorbent garment has a rear portion, a front portion and a crotch portion therebetween, in which the rear portion and the front portion are united together by a seam. The seam is constituted by a line of attachment passing through the outer edges of the front and rear portions at each side of the garment. To allow opening of the article by tearing, the front portion is provided with a line of weakening at either side, at a location spaced inwardly from the seam. Also, a re-closure possibility (i.e. releasable fastening means) is provided by two additional side panels on the front portion. A first edge of each of the side panels is fixedly attached to the outside of the front portion in the same seam as used for the rear and front portions, and a second edge of each side panel is provided with releasable attachment means which can releasably attach to the front portion.

GB-A-2 267 024 presents several disadvantages. Firstly, in order to prevent the front and rear portions of the diaper from separating involuntarily due to the forces arising due to the wearer's movement which act directly on the seams from inside the product, the seam has to be made particularly strong. Bonding using a force of 100 g/inch (393.7 g/cm) or more is thus required. At the same time, the line of weakening in each of the front portions has to possess a force of rupture below the bonding force level in the side seams, to avoid the seam being pulled apart when opening the diaper, yet still sufficiently high to prevent the line of weakening from being ruptured involuntarily.

The balance between these forces is difficult to achieve reliably, especially in high-speed production, particularly since the seam has to extend through three layers of material. Producing a reliable seam extending through all three separate layers of the product adds a further difficulty to be taken into account when producing the required bond strength.

Still further, the releasable attachment means on the front portion side flaps is releasably attached to the front portion of the product with a strength which should prevent the product from coming apart involuntarily when only the front portion side flaps are used to hold the product together. Due to this arrangement, when the front portion is to be pulled away from the rear portion at the lines of weakening, the releasable attachment means will exert a force on their line of attachment in the seam unless the reclosable means is first undone. This force may rupture the seam between either the front and rear portions or the front portion and the front side flaps.

A further known solution using a flush and welded connection between two side portions of a diaper is disclosed in U.S. Pat. No. 5,370,634. The flush seal is subject to peel forces arising from the normal movements of the wearer. Likewise the sealed area presents outwardly extending edge portions which are sealed at their outermost edges, thereby producing relatively hard combined edge portions. This is not only unsightly, but the hard free edge can easily come into contact with the user's skin at the upper and or lower edges thereof, causing discomfort.

The seam produced in GB-A-2 267 024 also has further disadvantages in that not only two, but three panels are combined with their outer cut edges lying outside the seam. As in U.S. Pat. No. 5,370,634, this produces a stiff edge arrangement, since the seam lies just inside the edges of the three panels. This again can affect comfort when the wearer's clothes press against the hard seam edge for example, as well as resulting in discomfort at the upper and lower edges of same. The flush seams in both U.S. Pat. No. 5,370,634 and GB-A-2 267 024 nevertheless allow production in a flattened condition.

WO-A-99/65438 discloses a further garment arrangement in which the outer edges of a front waist section are overlapped by two rear side panels of a rear waist portion. The outer ends of the front waist portion are fixedly attached by means of passive bonds to the inner surface of the rear waist portion and to the leg elastic at the rear part of the garment. The rear side panels further comprise two different type of reclosure means in the form of hook and loop fasteners which are releasably secured to the front waist portion. In this way, the passive bonds provide added shear strength to assist the reclosure means. Such an arrangement can provide a stable side closure system as a result of the passive bond locations. However such products suffer from a lack of adaptability and poor comfort and must rely on the waist band to provide some limited elasticity.

The invention has the object of providing an absorbent product with an improved side closure construction which allows low attachment forces to be used in releasable and non-releasable (i.e. fixed) attachment areas, while maintaining a closure arrangement which is reliable yet which allows a high degree of elasticity in the side closure and at the same time providing a good fit on the wearer.

The present invention also seeks to provide a method for producing an absorbent article of the type described above which obviates the problems with a flush seam and yet which can be easily formed in a flat condition during production.

SUMMARY OF THE INVENTION

In accordance with the invention, the absorbent product comprises at least two sets of closure means, a first closure means which forms a fixed attachment between the elastic side flaps of the front and rear portions by means of a weld, and a second closure means which is in the form of a releasable fastening means.

The fixed attachment by means of a weld refers to a type of permanent attachment between two parts which is not intended to be opened unintentionally and once opened cannot be reformed. The weld is preferably formed by ultrasound welding or by heat welding, but other forms of welding may be used. The weld may be such that it can be opened by applying peeling forces which results in peeling apart (typically with some tearing) of the weld, or may be made at a strength such that the weld remains substantially intact while a specific part of the side flap adjacent the weld will be made to rupture.

The releasable fastening means is, on the other hand, a type of attachment which is capable of being opened and re-closed. Such releasable fastening means comprises two members which cooperate to give a releasable attachment when a relatively light pressure is applied forcing the two members together. Such releasable attachment means may be of the mechanical type. One form of such a mechanical fastener is the hook and loop type, whereby one member comprises material having hooks or other projections thereon (e.g. mushroom-head projections), and the other member comprises complementary loops, receiving apertures or receiving spaces. Nonwoven material can for example by itself form a loop member, whereby the hooks of the complementary hook part can releasably attach to the nonwoven material. Many other types of releasable mechanical fasteners are known to one skilled in the art. A further type of releasable fastener may be an adhesive type of fastener, whereby a pressure sensitive adhesive is coated on one component and a complementary component is provided to which the pressure sensitive adhesive may adhere. Such releasable attachment means are well known in the field of absorbent products.

BRIEF DESCRIPTION OF THE DRAWINGS

The invention will now be explained in more detail with reference to certain non-limiting embodiments thereof and with the aid of the accompanying drawings, in which.

DETAILED DESCRIPTION OF THE PREFERRED EMBODIMENTS

Figure 1:
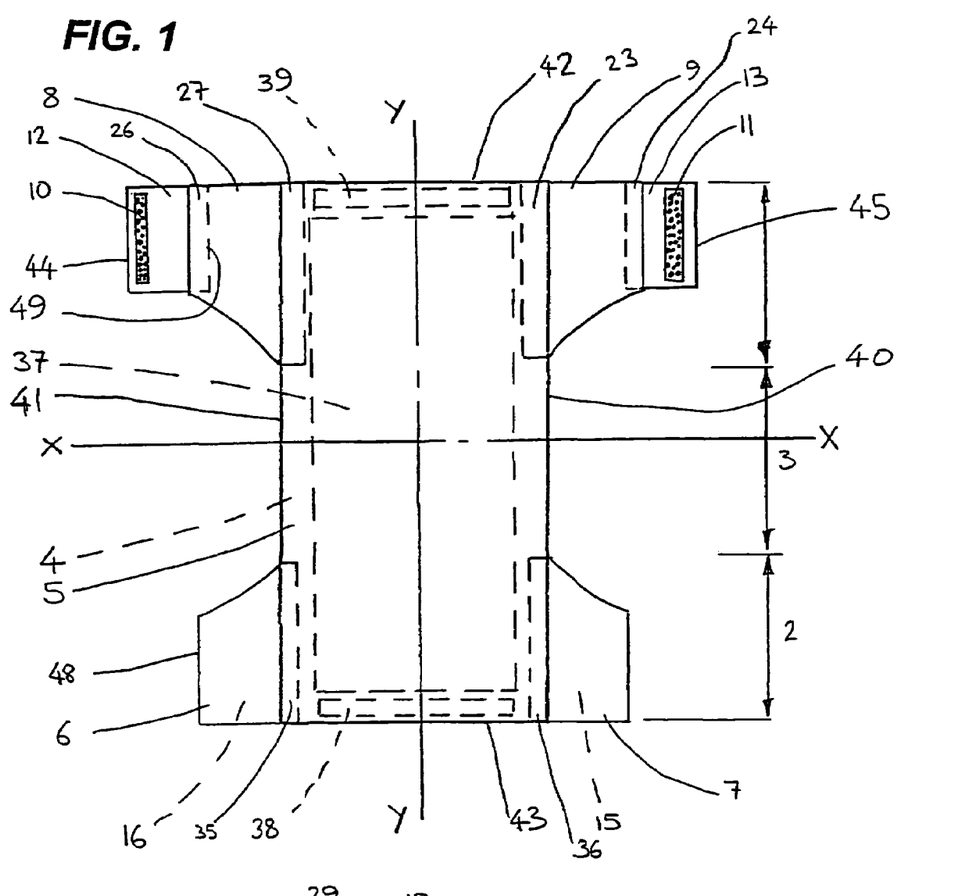
FIG. 1 shows a plan view of an absorbent product according to the invention in an opened-out condition, before the side flaps of the diaper have been fixedly attached together.

The absorbent product of the present invention is used for absorbing human exudate, such as a diaper or training pants. In particular, the present invention relates to absorbent pants of the disposable type, i.e., those which are to be discarded when soiled and are not intended to be washed and reused. In FIG. 1, the absorbent product is shown in a flattened state with the inner side of the absorbent product uppermost. The absorbent product comprises three portions, a rear portion 1, a front portion 2 and a crotch portion 3 extending between these portions. The length of the portions is not precise, but generally each of these portions occupies about one third of the length of the product in a flattened condition. The rear portion 1 has an edge 42 at its outer end and the front portion 2 has an edge 43 at its outer end. In the depicted condition, a longitudinal axis Y-Y and a lateral axis X-X are shown, these axes extending generally perpendicular to each other, the longitudinal axis extending generally between the middle of the rear portion 1 of the product and the middle of the front portion 2 of the product.

Throughout the present specification and claims, reference has been made to front and rear portions of an article. The rear portion of an article is that portion which is intended to be placed at the rear of a wearer in use, whilst the front portion is that portion intended to be placed at the front of the wearer during use. However, it will be apparent to one skilled in the art that the front and rear portions can be inverted and that the front and rear side flaps described below may thus be fitted to either of the front and rear portions without altering the underlying nature of the invention.

It should be observed that FIG. 1 depicts the absorbent product in a condition before the product has been fixed together in its final (prefastened) state, i.e. before the front side flaps 6, 7 and rear side flaps 8, 12 and 9, 13 have been overlapped and fixedly as well as refastenably attached together (the overlapped and attached arrangement will be explained further below).

The absorbent product includes an absorbent product chassis member comprising at least a back sheet 4 and a top sheet 5. The back sheet 4 is preferably impervious to liquids. The top sheet 5 is preferably a liquid permeable layer. Materials suitable for these layers are well known and typically the back sheet layer 4 may be formed entirely from or including a polyethylene (PE) film. Such a back sheet may for example be a textile-like back sheet formed from a laminate of PE and spunbonded polypropylene (PP) nonwoven material, where the PE has for example a surface weight between 12 g/m$^2$ and 20 g/m$^2$ and the PP has a surface weight between 10 g/m and 20 g/m$^2$. The top sheet layer 5 may be formed from a nonwoven polypropylene (PP) fibrous web (e.g. a spunbonded PP web) for example. Sandwiched between the back sheet layer 4 and the top sheet layer 5 is an absorbent core 37, the absorbent core comprising a batt of e.g. cellulosic fibres, preferably mixed with superabsorbent material in a homogeneous, or layered distribution or in a distribution which varies in the depth direction and/or in the major plane of the core. The absorbent core may take many shapes and forms and may include several layers with differing properties so as to improve absorption characteristics. The back sheet and top sheet layers 4, 5 are preferably of equal size and are preferably sealed to each other around their peripheries in a manner known in the art.

Elasticated waistband means 38, 39 are preferably provided at each end of the absorbent product chassis member and serve to provide a means of improved comfort, fit and containment in the product. Such elasticated waistband means are well known in the art. The elastic waistband means 38, 39 are shown as lying outside the absorbent core 37, although it will be understood that they may partially cover the area bounded by the absorbent core 37. Similarly, the waistband means may extend up to the longitudinal side edges 40, 41 and/or up to the end edges 42 and 43.

Further known elements can of course also be included in the absorbent product even though these are not shown in the present Figures. Such elements may include, for example leg elastics to provide a better fit around the wearer's upper legs, standing gathers, edge gaskets as well as other barriers and seals to prevent leakage.

Two front side flaps 6 and 7 are provided. Each side flap is formed as a single piece in the embodiment shown in FIG. 1, although a plurality of pieces laterally or longitudinally in series, or a plurality of layers or panels e.g. in series or partially or fully overlapping, may be used to form each side flap. In a preferred embodiment, a single piece may be used comprising a plurality of layers, one of which is elastic. The side flaps are each formed with an elastic portion, such as provided by an elastic laminate. The elastic portion may extend so as to cover the whole area of flaps 6 and 7, but preferably should at least cover the area thereof which lies outside the edges 40, 41 of the chassis up to the laterally outward edge of the flaps 6 and 7. Each front side flap 6, 7 is fixedly attached (by welding, adhesive, stitching or other known methods of fixed attachment) to a respective side of the chassis member at attachment locations 35 and 36, preferably on to the external surface of the back sheet 4 as shown. However, it should be understood that the side flaps 6, 7 may be attached to the internal or external surface of the top sheet 5 or the internal or external surface of the back sheet 4 if desired, or to both the back sheet 4 and top sheet 5. A still further possibility is that either the back sheet 4 or the top sheet 5, or a part thereof, may itself be included as part of the side flaps and thus form one of the layers of material constituting the side flaps 6, 7, 8, 12, 9, 13, as explained below in respect of a further embodiment.

Figure 3:
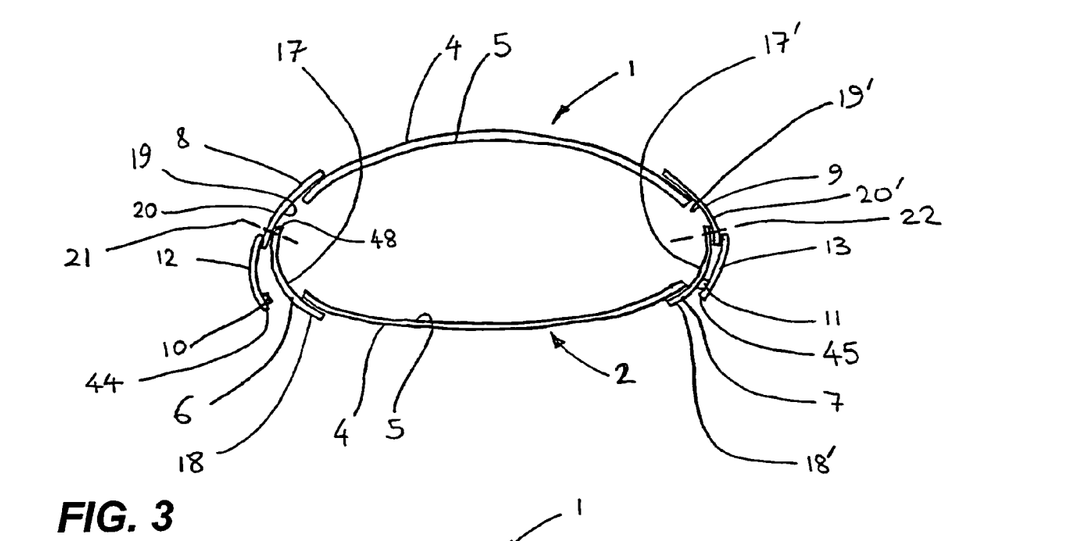
FIG. 3 shows a view from above of an absorbent product according to FIG. 2, showing the connections of the various layers before rupture of the side attachments.

At the rear portion of the absorbent chassis, there are two rear side flaps 8, 12, 9, 13. In the preferred embodiment shown, the rear side flaps are separate flaps comprising a first portion 8, 9 and a second portion 12, 13. The second portion 12, 13 is fixedly attached (by welding, adhesive, stitching or other known methods of fixed attachment) to the respective first portion 8, 9 at attachment locations 26 and 24 respectively on the external surfaces 20, 20' of the first portions (FIG. 3). Each second portion 12, 13 is fixedly attached at a location laterally outwardly of the attachment locations 23 and 27, such that the second portions 12, 13 lie laterally outwardly with respect to the rear side flap first portions 8, 9.

Each of the second portions 12, 13 in such a structure is not intended to lie directly against the skin of the wearer (see FIG. 3 explanation below) and thus the second portions 12, 13 may be formed stiffer than the first portion, e.g. by using a stiffer material for the second portions 12, 13. The second portions are each preferably formed to be inelastic. Being inelastic allows the second portions 12, 13 to provide a more stable panel structure while avoiding any folding or wrinkling effects for example.

An arrangement with two portions 8, 9 and 12, 13 is not however limiting for the invention, as long as a portion of the flaps are elastic. Thus, the rear side flaps may each be composed of only a single portion, or in a further embodiment of three or more portions. Each of the rear side flaps is fixedly attached (by welding, adhesive, stitching or other known methods of fixed attachment) to a respective side of the chassis member at attachment locations 23 and 27, preferably on the external surface of the back sheet 4 as shown. However it should be understood that the side flaps 8, 12 and 9, 13 may be attached to the internal or external surface of either the top sheet 5 or the back sheet 4 as desired, or to both the back sheet 4 and the top sheet 5.

In the preferred embodiment shown using two portions, at least a substantial part of the area of the first portion 8, 9 is formed of elastic material, and preferably the whole area of the first portion 8, 9 is formed of elastic material, such as an elastic laminate material. In a more preferable embodiment which avoids waste of elastic material without reducing elasticity, the elastic material is placed in that area of the first portion 8, 9 lying outside the attachment zone 23, 27 up to the attachment zone 24, 26 (i.e. in the portion of the flap which is free for elastic extension).

Each of the rear side flaps carries one member of a releasable fastening means 10, 11 at its outer end. Each member 10, 11 of the releasable fastening means in the shown embodiment is preferably constituted by a hook-type member preferably in the form of a strip of hook-type material extending between the upper and lower edges of the second portions 12 and 13 of the rear side flaps. Although a single strip is shown, several strips may instead be used, which can then be intermittently spaced from one another, preferably in a vertical direction. Similarly, the vertical extent of the members 10, 11 is shown as preferably extending almost the whole longitudinal length of the side flap portions 12, 13 leaving a suitable distance from the upper and lower edges of the flap portions for manufacturing tolerances. Preferably the longitudinal length of members 10, 11 on the rear side flaps is between 25% and 75%, preferably between 25% and 60%, of the longitudinal length of the front side flaps 6, 7 at the intended attachment location thereon. This is intended to substantially avoid any contact of the member 10, 11 with the body. The members 10, 11 may however extend the whole length of the flap portions 12, 13.

It is however preferred that where hook and loop members are used, the loop member of the releasable fastening means should have a larger surface area than the hook member.

Similarly, the second portions 12, 13 of the rear side flaps may be formed entirely of nonwoven loop material, requiring thereby that a hook member be positioned on the outer surface of the inner (front) side flap in the overlapped condition.

These members 10, 11 are adapted to releasably engage with corresponding members 15, 16 of the releasable fastening means on the front side flaps 6 and 7. Since the second portions 12, 13 are preferably made relatively stiff compared to the first portions, as explained above, this will allow the second portions 12, 13 to provide a more stable base for the strip members 10 and 11 and thus can assist in forming a more reliably attached and more easily handled releasable fastening arrangement.

In the embodiment shown, the front side flaps themselves include an external covering material to which the members 10, 11 can releasably be fastened, although, if desired, separate additional strips of material, e.g. loop material pieces (not shown) may be added. An example of an elastic laminate suitable for this purpose will be explained further below with regard to FIG. 5.

Although it is shown in the drawings that the front and rear side flaps are separate pieces from one another, it will however be understood by the skilled person that the front and rear side flaps on each respective side of the chassis member may be formed as a single continuous member, attached along the entire respective side edges 40, 41 of the chassis member. Alternatively, the rear side flaps and the front side flaps may remain as separate members in the manner shown in the Figures, but may be extended in the longitudinal direction to simply overlap each other in the area of the crotch region 3.

Similarly, although the rear side flaps 8, 12 and 9, 13 and the front side flaps 6, 7 are shown as being separate members fixedly attached at respective longitudinal side edges 40, 41 of the chassis member rear portion 1 and front portion 2, the rear side flaps could alternatively be combined as a single separate piece (not shown) extending laterally across the rear portion 1 and extending as side flaps beyond the longitudinal side edges 40, 41 of the chassis member. Similarly the front side flaps 6, 7 could be formed by a single separate piece (not shown) attached laterally across the front portion 2 of the chassis member.

In order to form the absorbent product of the invention, a fixed, preferably welded attachment is provided between the front side flaps 6, 7 and the respective rear side flaps 8, 12 and 9, 13 in the prefastened condition. In order for this to occur, the chassis member is preferably folded at some stage, substantially along or parallel to the lateral axis X-X, such that the front and the rear side flaps can overlap. In an alternative embodiment, the front side flaps and rear side flaps can however be made to first overlap and then be welded, before folding of the chassis member, and then the rear and/or front side flaps attached to the chassis. This is also explained with respect to the various steps and various order of steps of manufacture described further below.

The form of the overlap is an important factor in providing good seam security, good comfort and allowing a high degree of elasticity. The preferred overlap is shown externally in FIG. 2 and from above in more detail in FIGS. 3 and 4 for example. As these Figures show, each one of the front side flaps 6, 7 is fixedly welded to a respective one of said rear side flaps 8, 12, and 9, 13 such that the outer surface 18, 18' of each one of the front side flaps 6, 7 lies against the inner surface 19, 19' of a respective rear side flap 8, 12, and 9, 13.

Figure 2:
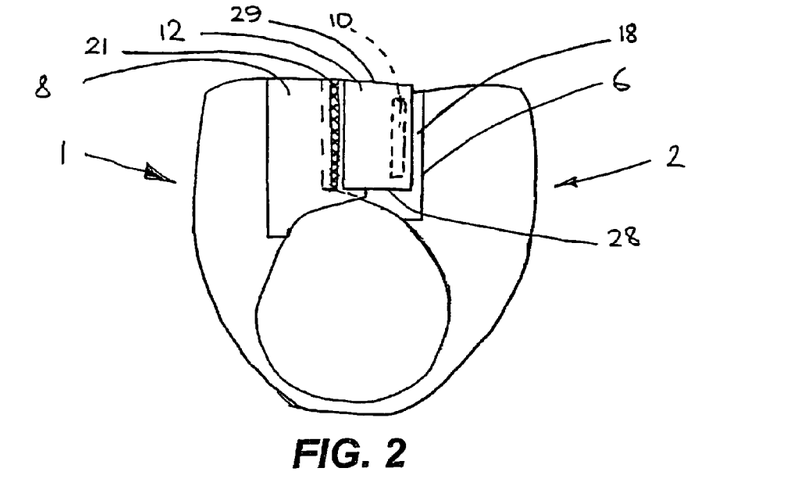
FIG. 2 shows a side view of an absorbent product according to the invention similar to that in FIG. 1, in which the side flaps having been fixedly attached together by means of a weld.

In FIGS. 2 and 3, it can be seen that the area of the weld 21, 22 is formed at the end portion of the first portions 8, 9 and the end portions of the corresponding front side flaps 6 and 7, so as to fixedly (i.e. non-releasably) join these portions together. In this regard the term "end portion" refers to that portion of each front side panel which overlaps each rear side panel first portion 8, 9. Such an overlap may be on the order of 0.5 to 3.5 cm and, preferably, between 0.5 and 2 cm.

In the closed condition as shown in FIG. 2, it can be seen that the releasable fastening means 10, 11 on the second portions 12 and 13 are already in contact with the corresponding fastening members 15, 16 of the outer surface 18, 18' of the front side flaps 6, 7. Thus a strong force is provided preventing separation of the front and rear side flaps, including the force provided by both the releasable fastening means 10, 11, 15, 16 and the welds 21, 22.

Since the flaps 6, 7 lie against the wearer's skin, it is preferable if the outer edges of these are formed so as to be soft. Where, for example, the front side flaps 6 and 7 are formed of an elastic laminate having nonwoven outer surface material such as spunbonded PP, this edge can clearly be soft without the addition of further outer end edge arrangements.

Moreover, due to the overlapping relationship of the front and rear side flaps, with the inner surface of one lying against, and welded to, the outer surface of the other, the forces acting from the wearer during movements (e.g. sitting, standing, etc.) to separate the front and rear side panels at the welds 21, 22 are not peeling forces as in much of the prior art, but instead are shear forces. Since it is easier to rupture an area of fixed attachment such as a seam by peeling than it is by applying shear forces, it will be apparent to one skilled in the art that it is extremely difficult to rupture the area of attachment in the present invention by the movements of the body. Therefore, a reliable seal is provided.

The provision of a reliable seal by this overlap structure thus allows attachment forces to be used which have a force value against peeling of less than 1000 g/inch (394 g/cm), as measured by the method disclosed in GB-A-2 267 024. Thus, attachment forces having a peeling strength force of less than 350 g/cm and, preferably, less than 300 g/cm, and more preferably, less than 200 g/cm can be used.

At the same time, it will be observed that in the preferred embodiments shown only two panels are included in the area of the welds 21, 22, namely the front side flaps 6, 7 and the rear side flap first portions 8, 9. This allows a reliable and easily controllable seam to be made. Furthermore, the product is more comfortable to handle and wear than products where the front and rear parts of the absorbent pants are attached at their sides in a flush arrangement, since there are no relatively rigid parts pointing outwardly. As discussed above, further panels can of course also be included.

In one embodiment, the second portions 12, 13 of the rear side panels are fixedly attached (by welding, adhesive, stitching or other known methods of fixed attachment) at attachment locations 26, 24 to the first portions 8, 9, which locations 26, 24 are laterally outward of the areas of welds 21, 22 as seen with respect to the lateral axis and with respect to the rear portion 1 of the chassis. However, it will be understood that the attachment locations 24, 26 may be laterally inward of the areas of the welds 21, 22 if desired, whilst still allowing only two panels to be used in the welds 21, 22. This can be arranged for example by fixedly attaching the panels 12 and 13 after first forming the welds 21, 22. The attachment area of portions 12 and 13 to portions 8 and 9 could however also be made to coincide with the welds 21 and 22 and the welds 21, 22 may also be made so as to extend through all three panels (i.e. front side flaps 6, 7, rear side flap first portions 8, 9 and second portions 12, 13). This is easily possible, although less desirable, since the strength of the weld for resisting peel forces need not be so great due to the provision of the overlapped inner and outer surfaces of the side flaps. It is preferred that no more than four material layers should be included in the welded regions, however, preferably no more than three, and most preferably only two material layers should be included. In whichever way the weld 21, 22 is formed, the weld is preferably placed laterally inwardly with respect to the releasable fastening means 10, 11 at the outer ends of the rear side flaps proximate the outer end edges 44, 45 thereof, such that the weld 21, 22 in each of the rear side flaps 8, 12, 9, 13 lies laterally inwardly with respect to the releasable fastening means 10, 11 positioned on its respective rear side flap.

In other words, for the embodiment shown in FIG. 3, where the rear side flaps 8, 12, 9, 13 overlap the front side flaps 6, 7, the rear flaps form an outer side flap and the front side flap forms an inner side flap of the whole side closure structure. The releasable fastening means 10, 11 is thus positioned closer to the outer edge 44, 45 of the outer flap than the weld 21, 22.

Also, the position of the weld with respect to the elastic portions is a factor in giving a maximum degree of elasticity to the side closure structure. In this regard the weld 21, 22 should preferably be positioned proximate the laterally outer edge of the elastic portion of at least one of the front and rear side flaps 6, 7, 8, 12, 9, 13. In this way, there is little or no elastic material which remains inactive outside the welds 21, 22 and thus the maximum amount of elastic material is available for providing the required elasticity in the side closures.

In the embodiment shown, the welds 21, 22 are positioned proximate the laterally outer edge 48 of each of the front side flaps 6, 7, each of the front side flaps being elastic. The welds 21, 22 are also placed proximate the laterally outer edge 47 of the elastic portion (first portion 8, 9) of each of the rear side flaps. In this way, the area of elastic material which is elastically inactive is kept to a minimum thereby allowing the maximum lateral extent of elastic material to be fully used in both front and rear side flaps. In terms of the meaning "proximate" in this regard, this means less than approximately 1.5 cm from the end edge of the elastic portion. It is, however, preferred if the distance is less than approximately 1 cm and still more preferable if the distance is less than approximately 0.5 cm.

As shown in FIG. 2, the weld 21 extends between the upper edge of front side flap 6 and the lower edge of the same. Preferably, the area of the weld extends the entire distance between these upper and lower edges and the line of weld tool application may even extend beyond the upper and lower edges. The attachment area may however be shorter, although the advantage with an extension all the way between the upper and lower edges is that the product has no loose side flap corners which may possibly fold over and become unsightly during storage. Similarly, a more secure/stable fit during use is obtained by arranging the weld to extend all the way between the upper and lower edges, which can be particularly relevant when the elastic portions are placed between the welds 21, 22 and each of the side edges 40, 41.

When the absorbent product, in the form of disposable pants as shown in FIG. 2, are to be inspected to check whether they have been soiled, or when they are to be removed entirely, it is convenient if the entire pants do not have to be removed over the wearer's legs and feet. Thus, the areas of attachment provided at welds 21, 22 simply have to be ruptured by being peeled open. This destroys the welded seal and does not allow reclosure thereof. This can be done in any suitable way, preferably however by gripping and pulling rearwardly the free edge of the side flap second portion 12, 13 lying in front of the releasable attachment member 10, 11 while at the same time holding the front flap 6, 7 with the fingers of the other hand. The attachment welds 21, 22 will thus be peeled open vertically by the application of peeling forces thereto.

Figure 4:
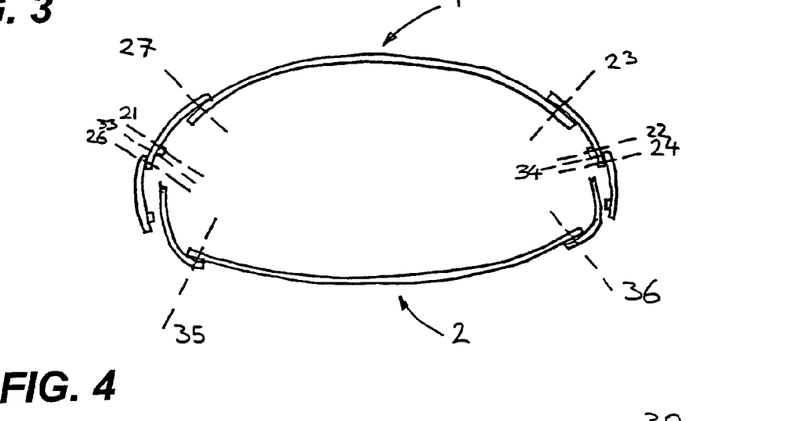
FIG. 4 shows a view similar to that in FIG. 3, of a product in which the front side flaps are additionally provided with lines of weakening which have been ruptured.

In an alternative embodiment shown in FIG. 4, a line of weakening 33, 34 can additionally be provided in each front side flap 6, 7, extending at least part way between the upper and lower edges of the respective front side flaps 6, 7 and at a location laterally outwardly of the respective attachment area 21, 22. In a manner similar to that described above, the front side panels and the rear side panels are separated, this time however by rupturing the front side flaps 6, 7 along the lines of weakening 33, 34. The lines of weakening in this regard may also be formed by the outer margin of the areas of welds 21, 22, for example, as a result of the welding process in which the outer edge of the weld can be made to provide a weakened area on the inner, front side flap 6, 7.

Whichever of the structures in the various embodiments is used, the absorbent pants will become separated at the side portions by rupture (either by peeling and/or tearing of the seals and/or by tearing of the front side flaps).

Once inspected, if the absorbent product is not soiled it can be re-attached while on the user by re-closing it. For this re-closure, the releasable fastening means 10, 11, 15, 16 are used, whereby the respective first member 10, 11 of the releasable fastening means is simply pressed into contact with the outer surface 18, 18' provided with the second member 15, 16 of the releasable fastening means. If desired, these releasable fastening members 10, 11, and 15, 16 may be attached and detached from one another several times.

While the side flaps may be formed of any suitable structure including an elastic portion, a preferred structure is one having nonwoven material 30, 32 on both the inside and outside surfaces thereof. In this way, the side flaps feel relatively comfortable against the skin of the wearer and at the same time provide an external surface to which one member 10, 11 of the releasable fastening means can attach. In a further embodiment (not shown) one or more of the layers of nonwoven material could be constituted by a nonwoven layer which is integrally included as part of the top sheet 5 and/or back sheet 4 structure.

Figure 5:
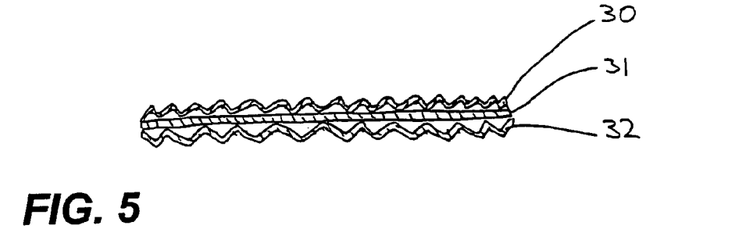
FIG. 5 shows a cross-sectional view through a laminate material which may be used in the front and/or side flaps.

In a particularly preferred embodiment, the front side flaps 6, 7 and/or the rear side flaps (i.e. portions 8, 9 only) may comprise an elastic laminate as shown for example in cross-section in FIG. 5. In such a laminate, a central elastic lamina material 31 is used. Such an elastic laminate may have an elastic extensibility at least in the lateral direction of over 100%, preferably over 150%, and even more preferably between 200% and 350%. Elastic materials able to produce this elasticity in the final laminate are well known in the art of absorbent products. These may include for example, elastomers made from block copolymers such as polyurethanes, copolyetheresters, polyamide polyether block copolymers, EVAs (ethyl-vinyl-acetates), elastomeric styrene-butadiene copolymers, tetrablock copolymers, including styrene-poly (ethylene-propylene) elastomeric block copolymers, polyamides, or natural and synthetic rubber materials, etc. One suitable elastomer is for example Extraflex™ CEX 802WR having a surface weight of 54 g/m², available from Tredegar film products.

Due to the overlapping nature of the front and rear side flaps, which may occupy between 0.5 cm and 3.5 cm lateral length in each side closure, the overlapped area will be relatively inelastic. Without high elasticity material constituting the side flap and having at least 100% elasticity (i.e. can be stretched elastically by more than 100% compared to its original length without substantial permanent strain), the elastic material of the respective side flaps lying between the overlapped panels and the edges of the chassis is not able to fully meet the requirements for good fit and comfort for all intended users.

Inelastic members used in this invention such as nonwoven materials, may comprise a continuous or discontinuous sheet, web, layer or fabric for example, which member can be stretched elastically by only small amounts, normally on the order of between 1 to 15%, but typically less than 10%. Such materials may be spunbonded, carded nonwovens or meltblown materials. The fibres can be e.g. polyolefins such as polypropylene or polyethylene. The fibres can also include mixtures of different polymers. Suitable nonwoven materials can also include several different nonwoven layers such as spunbond-meltblown-spunbond (SMS) laminates. A concrete example is a spunbonded material of polypropylene fibres where the material has a surface weight which can be arranged to lie between 12 and 30 g/m$^2$, and having a fibre thickness of between 0.5 and 5 dtex.

Attached on either side of the elastic lamina 31 in a stretched condition are relatively inelastic nonwoven material webs 30, 32. After attachment, when the elastic laminate is allowed to return to its relaxed state, the attached nonwoven webs contract and form a lightly corrugated surface, with air pockets between the corrugations, thus providing a comfortable feel.

In a variation (not shown) of the embodiment depicted in FIG. 5, the nonwoven material layer 30 or 32 of the side flap may be formed by an extension of the material in the top sheet 5 and/or the back sheet 4. For example, the back sheet 4 may be formed of a laminate structure (not shown) of a nonwoven material layer and a polymeric film material layer, whereby an extension of the nonwoven material layer of the back sheet could then be used to form either layer 30 or layer 32 of the side flap. Similarly, where one outer layer 30 or 32 is formed by nonwoven material of, e.g., the top sheet, the other outer layer 32 or 32 may be formed by nonwoven material of the back sheet or a separate sheet of material. Additionally, whilst the use of nonwoven materials is preferred, other inelastic materials can of course be used both in the top sheets and/or back sheets and then be extended so as to form at least one of the non-elastic materials in the side flaps.

The product of the invention may be formed in a variety of ways. However, in accordance with the present invention, a preferred method has been devised which allows the areas of attachment 21, 22 between the front and rear side flaps to be formed easily with the product lying in a flat condition. In this way, forming the areas of attachment 21, 22 is facilitated, especially where the area of attachment is formed by welding.

Figures 6A, 6B, 6C, 6D:
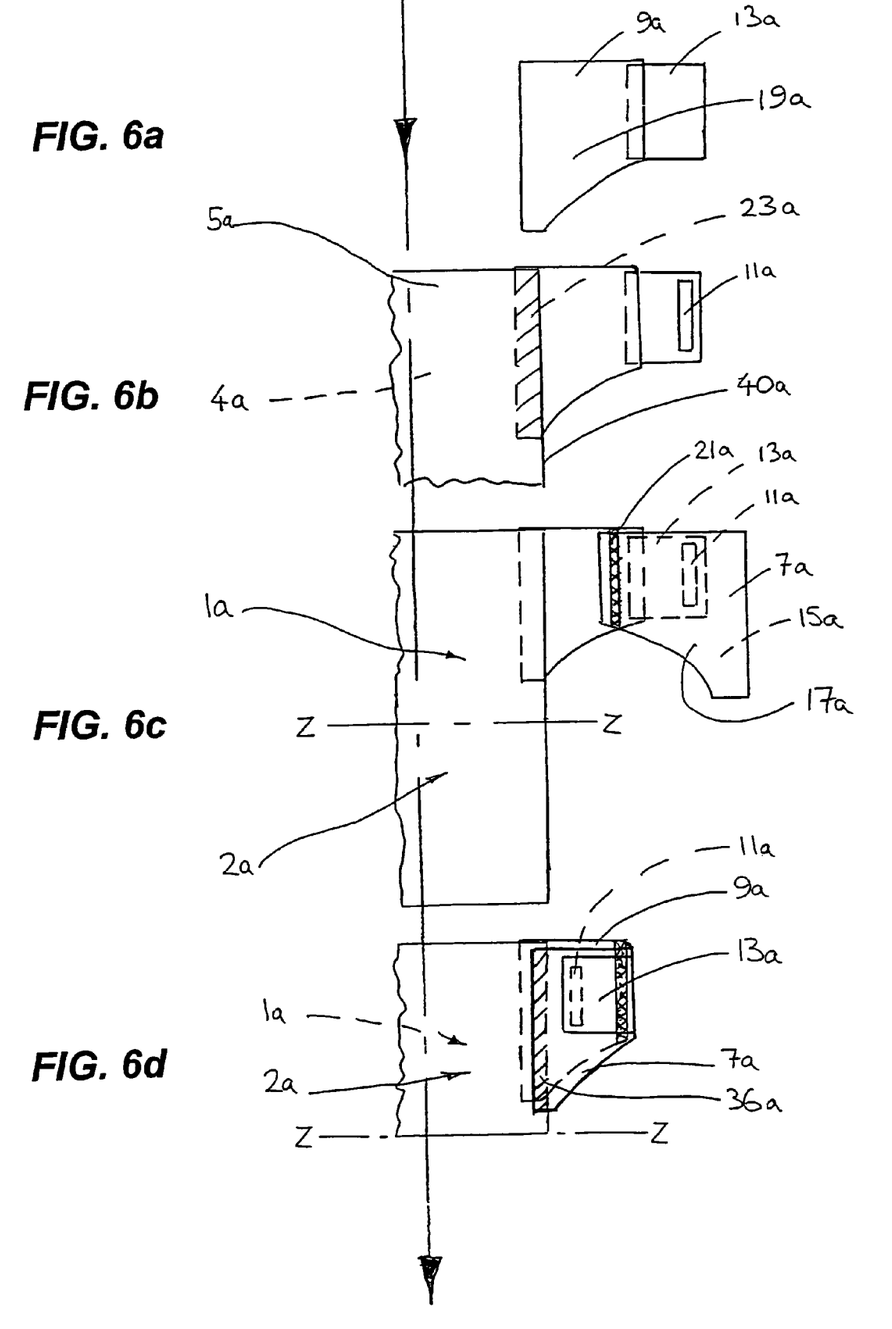
FIG. 6(a)-FIG. 6(d) show a series of steps, from top to bottom in the drawing, exemplifying the method of the present invention.

FIG. 6(*a*)-FIG. 6(*d*) shows a series of operations which are carried out to produce an absorbent product. Only one side of the product is shown although the operations on the opposite side are the same. The order of operations, although shown as steps (a) to (d), can however be varied to some degree as will be understood from the following.

In order to aid understanding, like reference numerals have been used to denote corresponding parts described with respect to the product of the invention, however with the addition of the letter "a" after the numerals.

The production flow is intended to be from step (a) to step (d) as shown in FIG. 6(*a*) to FIG. 6(*d*). In step (a) a first portion 9*a* of a first side flap member (e.g., rear side flap) is shown with its inner surface 19*a* uppermost and fixedly attached to a second portion 13*a*. The attachment of these two portions can occur at the moment they are placed one upon the other (e.g., by adhesive) or it can occur subsequently thereto such as by welding, for example.

In step (b), an absorbent product chassis member having a top sheet 5*a* shown uppermost and a back sheet 4*a* underneath, is laid on the first portion 9*a* and fixedly attached thereto at an area 23*a* at one end portion of the chassis member, such that it extends laterally outwardly from a side edge 40*a* of the chassis member. It is also possible, in an alternative embodiment (not shown), to arrange the first portion 9*a* to be located between the top sheet 5*a* and the back sheet 4*a* and thus conceal the joint 23*a* between the top sheet 5*a* and back sheet 4*a*. This can be done for example by first laying down the back sheet 4*a*, then attaching the flap portion 9*a*, then applying the absorbent core and then adding the top sheet 5*a*.

As will also be clear, the chassis member may however be placed first on the production line, followed then by the flap member 9*a*, 13*a* if desired, i.e., a reversal of steps (a) and (b). A first portion of a releasable fastening means 11*a* is added as a strip or the like, as described previously, to the end of the first (rear) side flap. This may be in either step (a) or step (b) for example.

In step (c) the second side flap member 7*a* is added (e.g., the front side flap 7), with its inner surface 17*a* upwards and its outer surface facing downwards, whereby the second member 15*a* of the releasable fastening means is on that downward facing side. In this condition, the inner surface 19*a* of the first side flap member 9*a*, 13*a* lies in an overlapping relationship against the outer surface of the second side flap member 7*a* in a flat (i.e., unfolded) state. The fixed attachment area 21*a* is then formed, for example by welding, at the rectangular area indicated by 21*a*, whereby it is noted that the weld extends between the upper and lower edges of the first and second side flaps.

At this stage, first end portion 1*a* (e.g., the rear end portion 1) and the second end portion 2*a* (e.g., the front end portion 2) of the chassis member are still in a flat condition. Thus, in order to form the closed product, the portion 2*a* needs to be folded on to the portion 1*a* and the second flap member 7*a* needs to be fixedly secured to the second end portion 2*a*.

This folding operation can be done either by starting at step (c) and then in step (d) folding portion 2*a* onto portion 1*a*, and then folding the second flap member 7*a* over the first flap member 9*a*, 13*a* and thus into contact with the outer (back sheet 4*a*) surface of end 2*a*. Alternatively, the second flap member 7*a* can be folded over the first flap member 9*a*, 13*a* and then the end portion 2*a* folded over on top of the outer surface of the second flap member 7*a*, and thus into contact with the inner (top sheet 5*a*) surface of end portion 2*a*.

In either condition, the end of the second flap member 7*a* is then fixedly secured at location 36*a* to the second end portion 2*a* of the chassis member. Preferably, such securement is performed by using adhesive on the cooperating surfaces of the flap member 7*a* and the second end portion 2*a* of the chassis member, although other methods of fixed attachment may also be employed.

In a still further embodiment, the attachment of the first flap member 9*a*, 13*a* to the second flap member 7*a* at the attachment area 21*a* (i.e., as in part of step (c)) can be performed without the chassis member being present. The chassis member can then be fixedly attached at attachment location 23*a* and attachment location 36*a*.

In a still further embodiment, before performing step (d), the flap 7a can first be folded before the chassis itself is folded, and only then attached at area 36a. In this way, the attachment 36a is positioned on the inside of the product and not visible.

Figure 7:
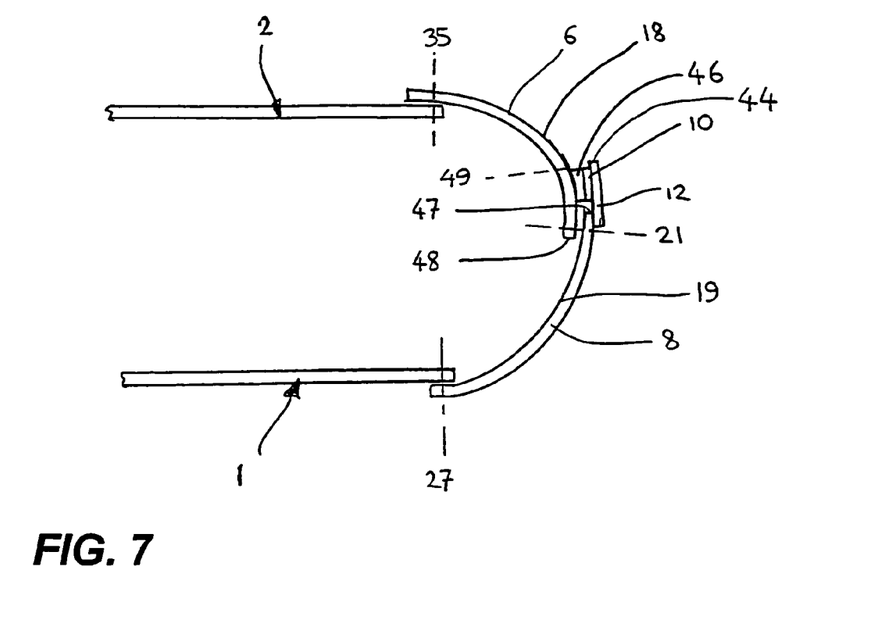
FIG. 7 shows a view from above, of one half of a further embodiment of a side closure arrangement.

FIG. 7 shows a further embodiment of the present invention in a view from above, similar to that in FIG. 3, wherein however only one side is shown (the other side being substantially a mirror image) and wherein the rear part 1 of the diaper is lowermost. In FIG. 7, the first side flap portion 8 and the front side flap 6 is elastic between the attachment location 27 and the end edge 47 and the attachment location 35 and the end edge 48 respectively, side flap 6 and first portion 8 preferably being formed entirely of an elastic laminate. The second portion 12 is preferably entirely inelastic. The front side flap 6 has, on its outer surface and fixedly attached thereto, one member 46 of a releasable fastening means in the form of a strip, the strip being elongate in the longitudinal direction Y-Y (i.e., in a plane perpendicular to the plane of the paper in the same way as members 10 and 11 as shown in e.g. FIG. 2 are elongate). The cooperating member 10 of the releasable fastening means is fixedly attached to the inelastic portion 12 of the rear side flap.

The weld 21 thus passes through the elastic portions proximate the distal (laterally outward) ends thereof. In this way, only two components need be attached together. Similarly, since the weld 21 is at the ends of each elastic portion in the small overlapped area between end edges 47 and 48, the elastic flap material between weld 21 and attachment location 27 remains active for elastic extension. In the first side flap 6, the portion thereof remaining active for elastic extension is, in this case, that portion which extends between attachment location 35 and the location 49 at which the laterally inner end of strip member 46 is attached to the side flap 6.

To further improve the amount of elastic material available for elastic stretching, the non-elastic portion of the side closure, i.e. between line 49 and weld 21, is preferably kept to a minimum. The distance between line 49 and weld 21 should preferably be configured such that this distance occupies a maximum of one third of the elastic part of the side closure (i.e., the distance between attachment location 35 and line 49 added to the distance between line 21 and attachment location 27, in the unstretched condition). Preferably, this distance should be between 0.5 and 3.5 cm. Similarly, in the unstretched condition, the length of the elastic portion (that portion between attachment locations 35 and 49 and between location 27 and weld 21) of the whole side closure, should preferably be greater than 75% of the length of the side closure (i.e., the distance between attachment locations 27 and 35 in the prefastened condition). The elastic extensibility of the side closure between locations 27 and 35 including the elastic and inelastic parts joined together, starting from a non-stretched starting length of the side closure, should preferably be greater than about 80% and most preferably greater than 100%.

If the member 46 is not present, the member 10 should thus attach directly to the outer surface 18 of side flap 6, and then the non-elastic portion would be between weld 21 and the location where member 10 attaches to the outer surface 18.

The member 10 can, for example, be of loop material and the cooperating member 46 of hook material, or vice versa. Inwardly facing hooks are however, preferable, since this allows easier disposal in a closed condition. It is also possible to construct the inelastic second portion 12 entirely of loop material and then construct member 46 of hook material to engage therewith.

Figure 8:
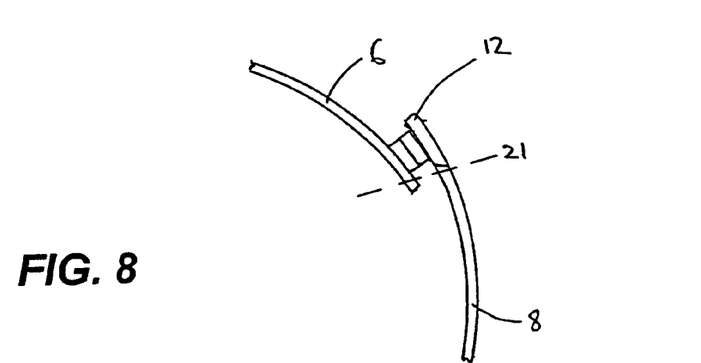
FIG. 8 shows a further embodiment in a view from above similar to that in FIG. 7, depicting the overlapped portions of the side flaps.
Figure 9:
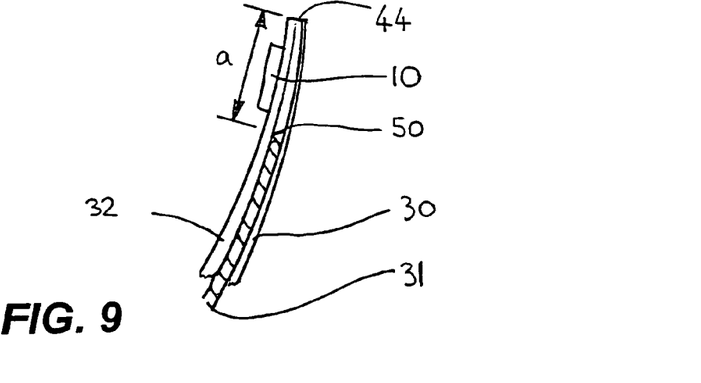
FIG. 9 shows an embodiment of the second (laterally outer) portion of the outer side flap in FIG. 8, in a view from above and enlarged.

FIG. 8 and FIG. 9 show a further embodiment of the invention, similar to that described in relation to FIG. 7, whereby the inelastic portion of the rear side flap (second portion 12) is formed not by a separate piece of material being attached to the outside of the first portion as in the embodiments of, for example, FIGS. 1 to 4, but instead by the elastic lamina 31 of the elastic laminate material (see also FIG. 5) being terminated at an end 50 which lies laterally inside end 44. Thus, distance "a" is inelastic and corresponds to the inelastic portion 12.

Figure 10:
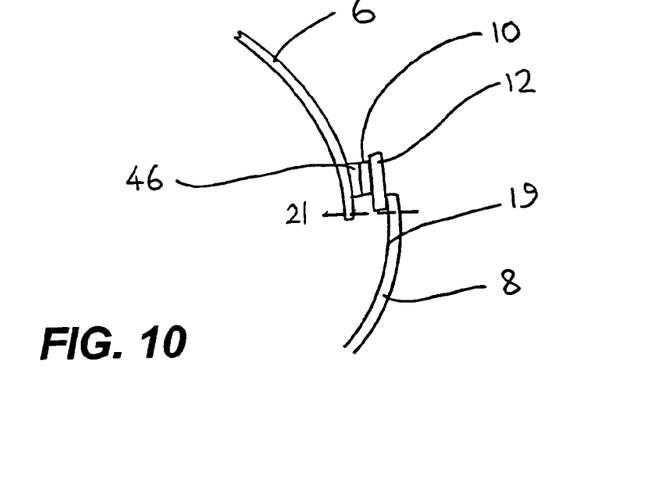
FIG. 10 shows a further embodiment of the invention in a view from above similar to FIG. 8.

In the embodiment shown in FIG. 10, this differs from that shown and described with respect to earlier embodiments in that the inelastic second portion 12 is located and fixedly attached to the inner surface 19 of first portion 8.

Figure 11:
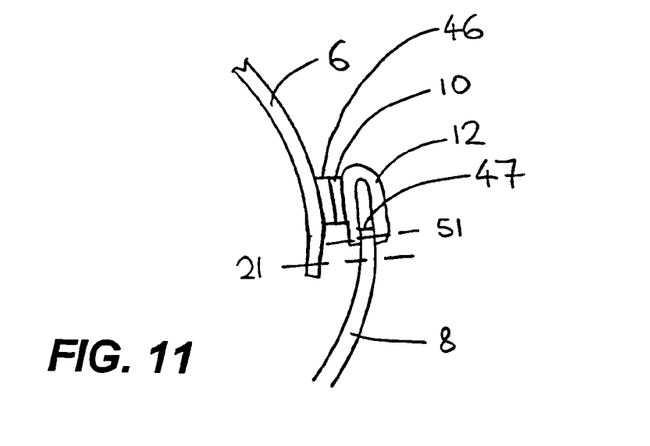
FIG. 11 shows a further embodiment of the invention in a view from above similar to FIG. 10.

In the embodiment shown in FIG. 11, the second portion 12 is formed as a U-looped strip, whereby the open ends of the "U" are fixedly attached, e.g., by welding or adhesive for example, to the laterally outer end 47 of the first portion 8 at attachment locations passing through line 51. In this way the second portion 12 will be more safely attached to the first portion 8 and the risk of separation of the portions 8 and 12 is reduced at the same time as providing a softer outer edge.

Figure 12:
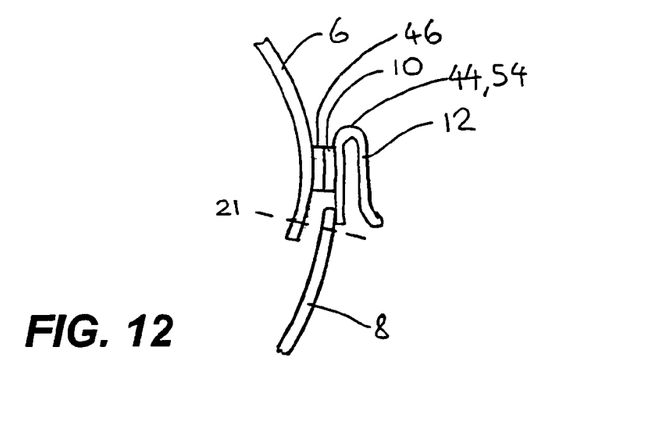
FIG. 12 shows a further embodiment of the invention in a view from above similar to FIG. 11.
Figure 13:
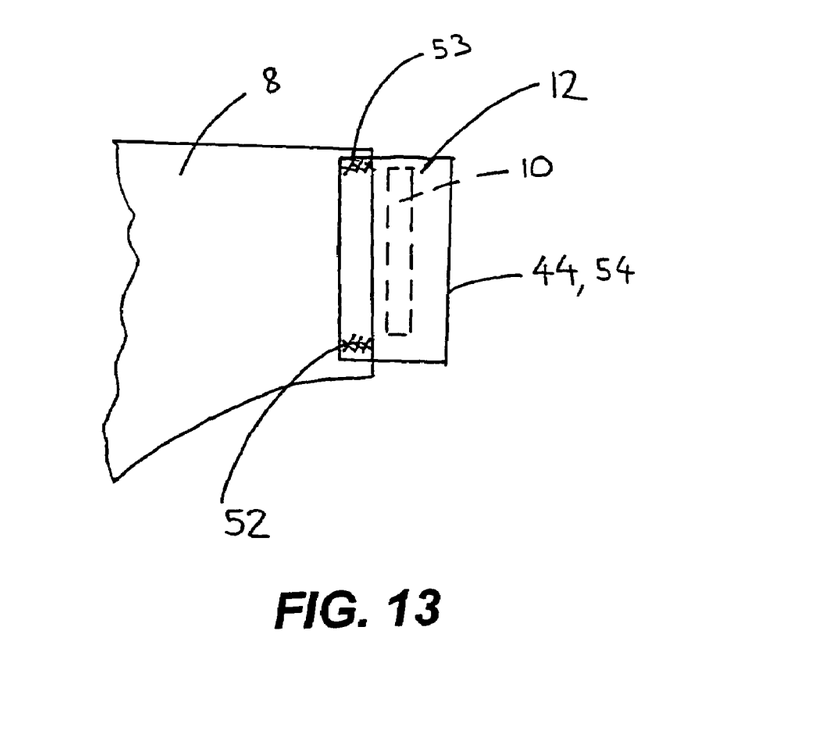
FIG. 13 shows a side view of the embodiment in FIG. 12.

In the embodiment of FIG. 12, a further possible form of the inelastic second portion 12 is depicted, in the form of a gripping pocket which allows the fingers of a hand to be inserted into the U-shaped loop for opening or refastening the product (the U-shaped loop being attached at e.g. its upper and lower longitudinal edges for example as shown in FIG. 13 at fixed attachment locations 52 and 53 (e.g. welds)). In this way, the user can insert one or more fingers between the attachment areas and use this as a gripping means to open the reclosable fastening means 10, 46 and/or as a means for peeling or tearing the first portion 8 away from the inner flap 6 at the weld 21. A user can similarly insert a finger between the round end 54 of the loop and the attachment locations 53 or 52 if the loop is made sufficiently long. As will also be apparent, either one of the two fixed attachments 52 or 53 could be omitted, which still allows a finger to be inserted into one corner area of the pocket. Many further modifications of such a gripping pocket by alternative means and locations of attachment will be apparent to a skilled person.

Figure 14:
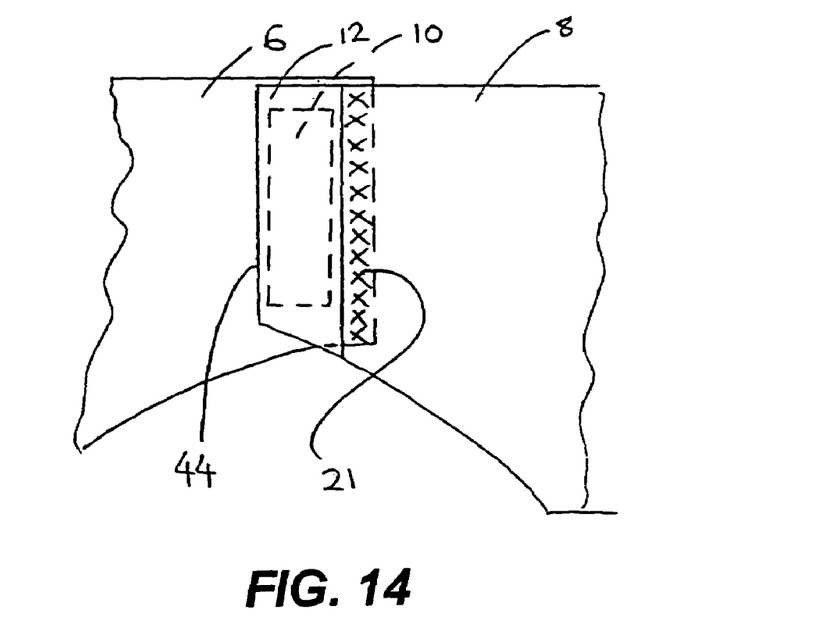
FIG. 14 shows a side view of a further embodiment of the overlapped side flaps.

In the embodiment of FIG. 14, which is a partial side view of the side closure showing overlapping panels 6 and 8, 12, the inelastic portion 12 is made to be gradually reduced in length moving laterally outwardly along the rear side flap 8, 12 to the end edge 44, so as to provide a laterally outwardly tapering lower edge. The member 10 may however maintain an elongate rectangular form. In this way a smoother transition between the lower edge of portions 8 and 12 is provided (when compared to e.g. the FIG. 1 embodiment) which provides a comfort improvement on the wearer's legs and reduces the amount of waste material at the same time.

Figure 15:
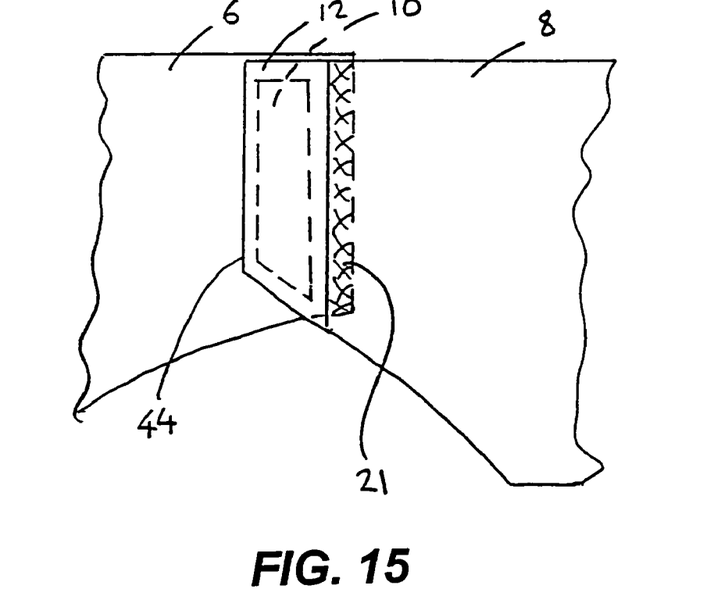
FIG. 15 shows a further embodiment in a view similar to that in FIG. 14.

The embodiment of FIG. 15 is similar to that of FIG. 14, differing however in that the member 10 is also made to taper towards the laterally outer edge 44. In this way, the second portion 12 can maintain the advantages described above and the member 10 can be spaced from the edges of the second portion 12 yet still use the maximum area for providing an attachment surface, which is particularly useful in allowing a more secure fastening when the weld 21 is broken.

Figure 16:
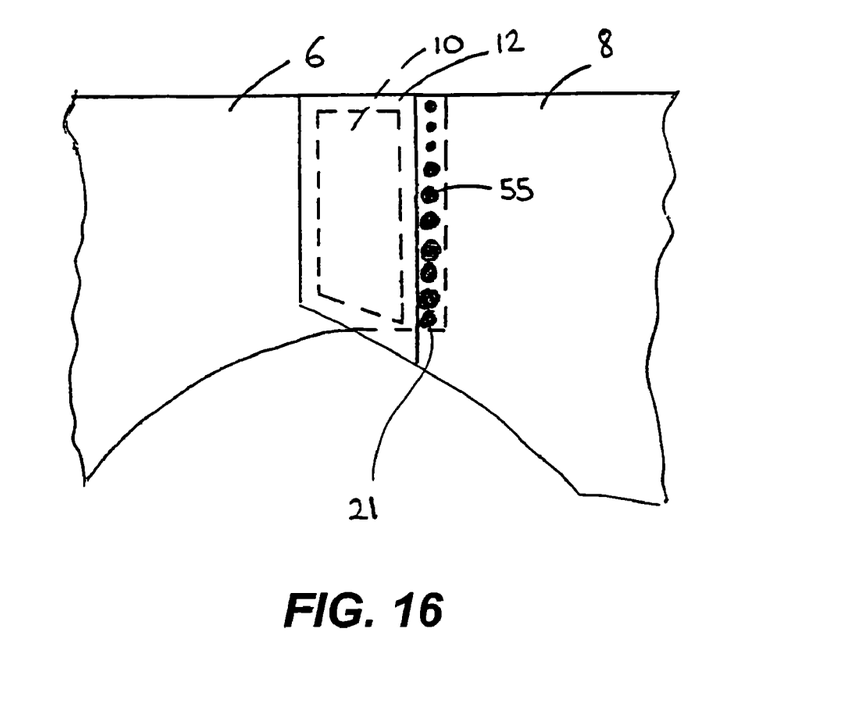
FIG. 16 shows a still further embodiment of the invention in a view similar to that shown in FIG. 15.

In the FIG. 16 embodiment, the fixed attachment in the form of weld 21 is formed by a series of weld points, e.g. spot welds 55, whereby the strength of the weld is made to increase from an upper edge of the side closure to a lower edge of the side closure. In this way, the weld 21 which forms the fixed attachment can be easily opened at the top edge, but still provides the overall required strength and the security to hold the prefastened product on the wearer. Additionally, this type of weld avoids the need for use of an intermittent tugging force being applied to open the weld when a helper removes the product from a child for example, which is typically the case with welds which are of the generally the same strength along the majority of their length. The strength is made to increase in FIG. 16 by using for example larger weld areas and/or increasing the proximity of adjacent weld points as seen in a direction moving from the upper edge to the lower edge.

Various alternative forms of welds 21, 22 may be used to form the fixed attachment between the side flaps, in which a pattern of weld bonding points is used (e.g. such as bonding points in the form of spot welds 55 as in FIG. 16). A "welded area" can be defined as being the smallest rectangle which encloses all the individual surface areas of the weld bonding points. In order to provide superior opening properties of the weld when desired, the combined individual surface areas of all the bonding points in a welded area should preferably be made to be less than approximately 50% of the welded area as defined by the rectangle. This may also be used in the case shown in FIG. 16 and other embodiments of course. In preferred embodiments, the combined individual surface areas may be less than 40%, less than 30%, less than 20% or even less than 10% of the welded area defined by the rectangle.

Figure 17:
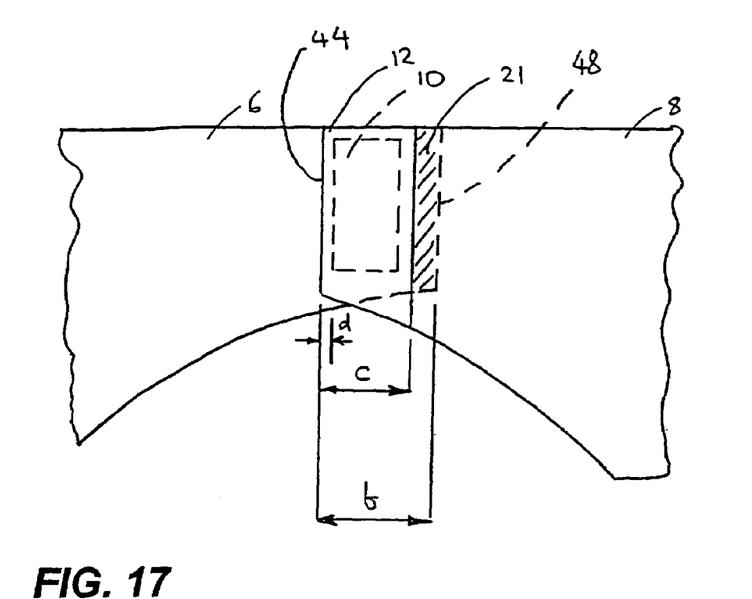
FIG. 17 shows an embodiment of the invention similar to that shown in FIG. 15, depicting particular dimensions, FIG. 18 (a) and FIG. 18(b) show two steps (a) and (b) of a test method for measuring peel strength.

In FIG. 17, the overlapping side panels 8, 12 and 6 are again depicted and a distance "b" has been indicated. The distance "b" is the total overlapping width of the two laterally outer end edges 44 and 48 of the rear and front side panels respectively. This distance "b" should preferably lie between approximately 0.5 cm and 4 cm, more preferably between 0.5 cm and 3 cm, and even more preferably, between 0.5 cm and 2 cm. Similarly, the width "c" of the second portion 12 should preferably be greater than 50% of the overlapping width "b". In such a way, the amount of elastic material which is not active elastically is minimised.

FIG. 17 also indicates a further distance "d" between edge 44 and the laterally outer edge of element 10 attached to second portion 12. This distance may be defined as a gripping distance "d". The gripping distance is the distance which can be used to grip the end of the second portion in order to open the reclosable fastening (formed by members 10 and 18 or 10 and 46 for example) between front and rear side panels. Distance "d" should preferably be less than 7 mm in order to prevent younger users from trying to open the reclosable fastening. To provide additional protection against opening a gripping distance of less than 5 mm or even less than 3 mm can be used. However, different levels of opening force should be observed in order to provide child safety features yet still allow opening in a reliable manner by most adult helpers, and in a comfortable manner for the wearer.

Experiments on this matter have shown that a child-safe closure can be produced when a gripping distance of up to 7 mm is used, wherein the reclosable fastening should have an opening force against peeling of above 4 N, preferably above 6 N, more preferably above 8 N and even more preferably above 10 N. With a gripping distance below 3 mm, it is preferable to avoid an opening force above 10 N. However, at the same time, the opening peeling force on both the reclosable attachment and also the weld 21 should preferably not exceed 20 N, otherwise the wearer is subjected to an intermittent tugging force being applied in order to open the reclosable fastening and/or weld 21, which is clearly unpleasant. Below 20 N, it has now been shown that such intermittent tugging forces are minimised if not entirely avoided, yet at the same time still provide the required level of force for a safe closure. Even more preferred are arrangements where the maximum opening force is below 15 N.

Figure 18A:
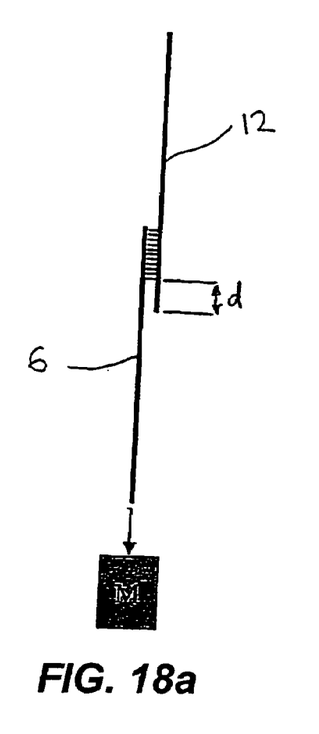
Figure 18B:
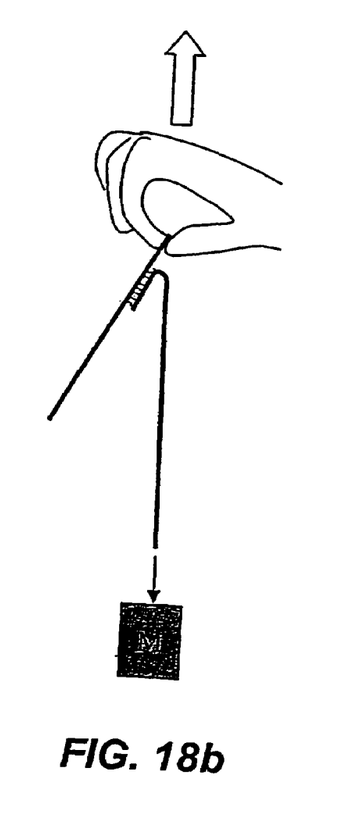

In order to measure the forces required to open a joint in peel (i.e. using peel forces), the test method as illustrated in the steps of FIG. 18(a) and FIG. 18(b) is used. The two parts of the closure (e.g. side flap 6 and second portion 12) are attached together e.g. by the reclosable fastening, and a weight is attached to one of the parts e.g. by being clamped to the part over its width. The gripping distance portion "d" is then gripped and lifted slowly and smoothly, in such a way that no jerky movements cause the reclosable joint to separate. If the weight can be lifted and the joint maintained in the situation shown in FIG. 18(b) for more than 30 seconds, it is judged that the joint can support the weight and thus meets a particular level of force determined by the weight. Whilst test machines could be employed to carry out this test, it is important to realise that the test should correspond as far as possible to a real-life situation and thus the test explained above is not only reliable and repeatable but is preferred over any machine test method.

Figure 19:
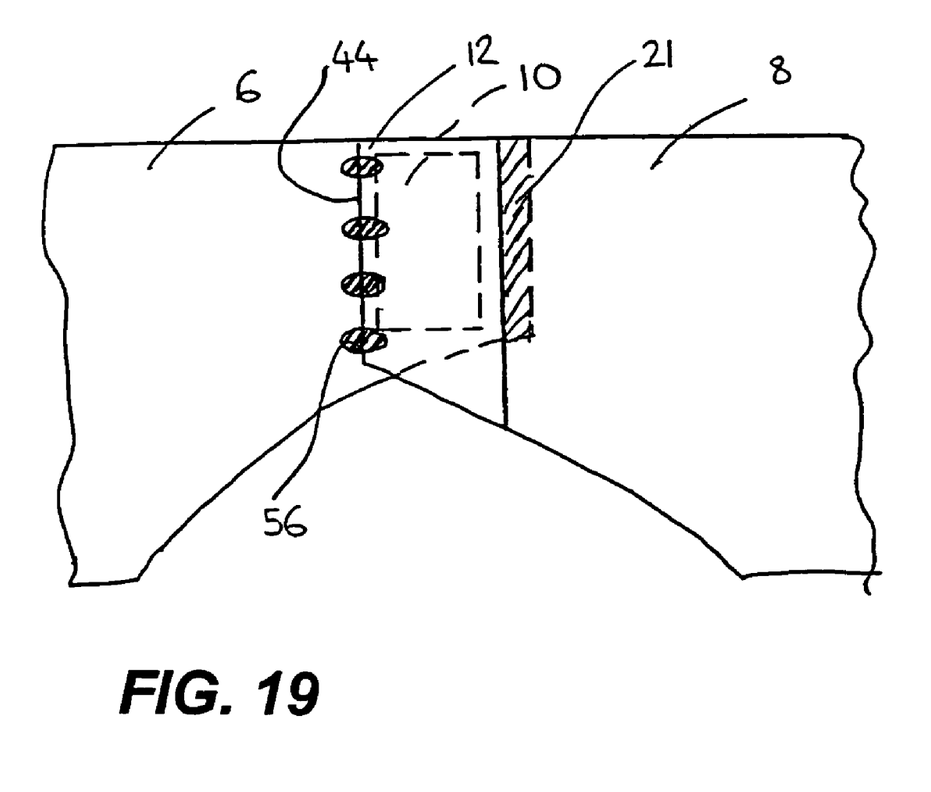
FIG. 19 shows a further embodiment of the invention in a view similar to that shown in FIG. 17, provided with an additional child-safety closure.

FIG. 19 shows a further embodiment of the invention in which increased child safety is provided by arranging one or more additional welds 56 at the outer edge 44 of the rear side flap (i.e. at the outer edge of the second portion 12 thereof, in this embodiment). These welds 56 in particular give the appearance of being permanently closed and so provide a psychological as well as a physical obstruction for a child user.

In the aforegoing, a number of embodiments have been described in order to illustrate different aspects of the invention. It is however to be understood that the individual features of one embodiment may however be used with, or in place of, features of another embodiment. In particular, features shown primarily in embodiments of the product per se are clearly to be understood as being included as additional features or alternative features in the method of the invention.

Further embodiments of the product and variations of the method will be readily understood by the skilled person upon reading the aforegoing and are intended to be encompassed within the scope of the invention as defined by the appended claims.

The invention claimed is:

1. A method of producing a prefastened, reclosable absorbent product, comprising: fixedly attaching a first side flap member at a first attachment location to an outer surface of a first end portion of an absorbent product chassis member, so as to extend laterally outwardly from a side edge of said chassis member, said first side flap member being provided with one part of a releasable fastening means, and welding a second side flap member at an area of attachment to said first side flap member such that an inner surface of said first side flap member is attached in an unfolded overlapping relationship to an outer surface of said second side flap member, folding said second side flap member over said first side flap member such that an inner surface of the second side flap member faces said inner surface of said first side flap member, and fixedly attaching said second side flap member to a second end portion of said chassis member.

2. The method according to claim 1, wherein said second side flap member is folded over said first side flap member after said second end portion has been folded onto said first end portion, and said second side flap member is then folded onto, and fixed to, an outer surface of said chassis member.

3. The method according to claim 1, wherein said second side flap member is folded over said first side flap member before said second end portion has been folded onto said first end portion, and said second side flap member is fixed to an inner surface of said chassis member.

4. The method according to claim 1, wherein said first side flap member is attached to said outer surface of said first end portion after said area of attachment is formed between said first side flap member and said second side flap member.

5. The method according to claim 1, wherein said first side flap member is a rear side flap provided with a first member of a releasable fastening means, and said second side flap member is a front side flap provided with a second member of said releasable fastening means, said second member cooperating with said first member and allowing releasable fastening.

* * * * *